United States Patent [19]

Zhang

[11] Patent Number: 5,546,942

[45] Date of Patent: Aug. 20, 1996

[54] ORTHOPEDIC ROBOT AND METHOD FOR REDUCTION OF LONG-BONE FRACTURES

[76] Inventor: Zhongman Zhang, 2190 Deer Creek Dr., Fayetteville, Ark. 72703

[21] Appl. No.: 258,002

[22] Filed: Jun. 10, 1994

[51] Int. Cl.⁶ .................................................. A61B 6/03
[52] U.S. Cl. ........................ 128/653.1; 606/57; 606/105; 395/97; 395/924
[58] Field of Search .................... 128/653.1; 606/53, 606/201, 97, 105, 57, 54, 86; 378/62, 21; 364/413.13, 413.14, 413.01; 602/32, 36, 39; 395/97, 924

[56] References Cited

U.S. PATENT DOCUMENTS

| | | | |
|---|---|---|---|
| 4,471,768 | 9/1984 | Ciullo | 128/83 |
| 4,485,815 | 12/1984 | Amplatz et al. | 606/185 |
| 4,558,697 | 12/1985 | Wu | 606/86 |
| 4,979,949 | 12/1990 | Matsen, III et al. | 606/53 |
| 5,013,317 | 5/1991 | Cole et al. | 606/96 |
| 5,133,342 | 7/1992 | Seaton | 602/39 |
| 5,154,171 | 10/1992 | Chirife | 607/24 |
| 5,236,432 | 8/1993 | Matsen, III et al. | 606/88 |
| 5,343,385 | 8/1994 | Joskowicz et al. | 364/413.01 |
| 5,397,323 | 3/1995 | Taylor et al. | 606/130 |
| 5,408,409 | 4/1995 | Glassman et al. | 364/413.13 |
| 5,410,638 | 4/1995 | Colgate et al. | 395/97 |
| 5,441,505 | 8/1995 | Nakamura | 128/653.1 |

FOREIGN PATENT DOCUMENTS 469996  2/1992  European Pat. Off. ................. 606/54

Primary Examiner—Krista M. Zele
Assistant Examiner—Brian L. Casler
Attorney, Agent, or Firm—Kenyon & Kenyon

[57] ABSTRACT

An apparatus and method are provided for the reduction of bone fractures. The apparatus includes an x-ray imaging system which compares the fractured bone with an unfractured bone, a robot controller which controls a robot hand so as to move the fractured bone in response to a command from a physician, and a safeguard system to detect abnormal tension in the limbs which can sound an alarm and cease robot motion if an error is detected. The method includes the comparison of x-ray images of unfractured and fractured bones and the movement of a robot hand grasping a fractured bone in a direction suitable for effective bone reduction.

40 Claims, 7 Drawing Sheets

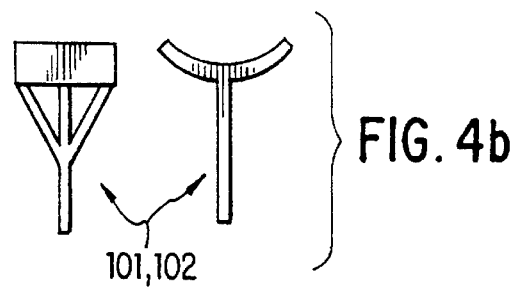
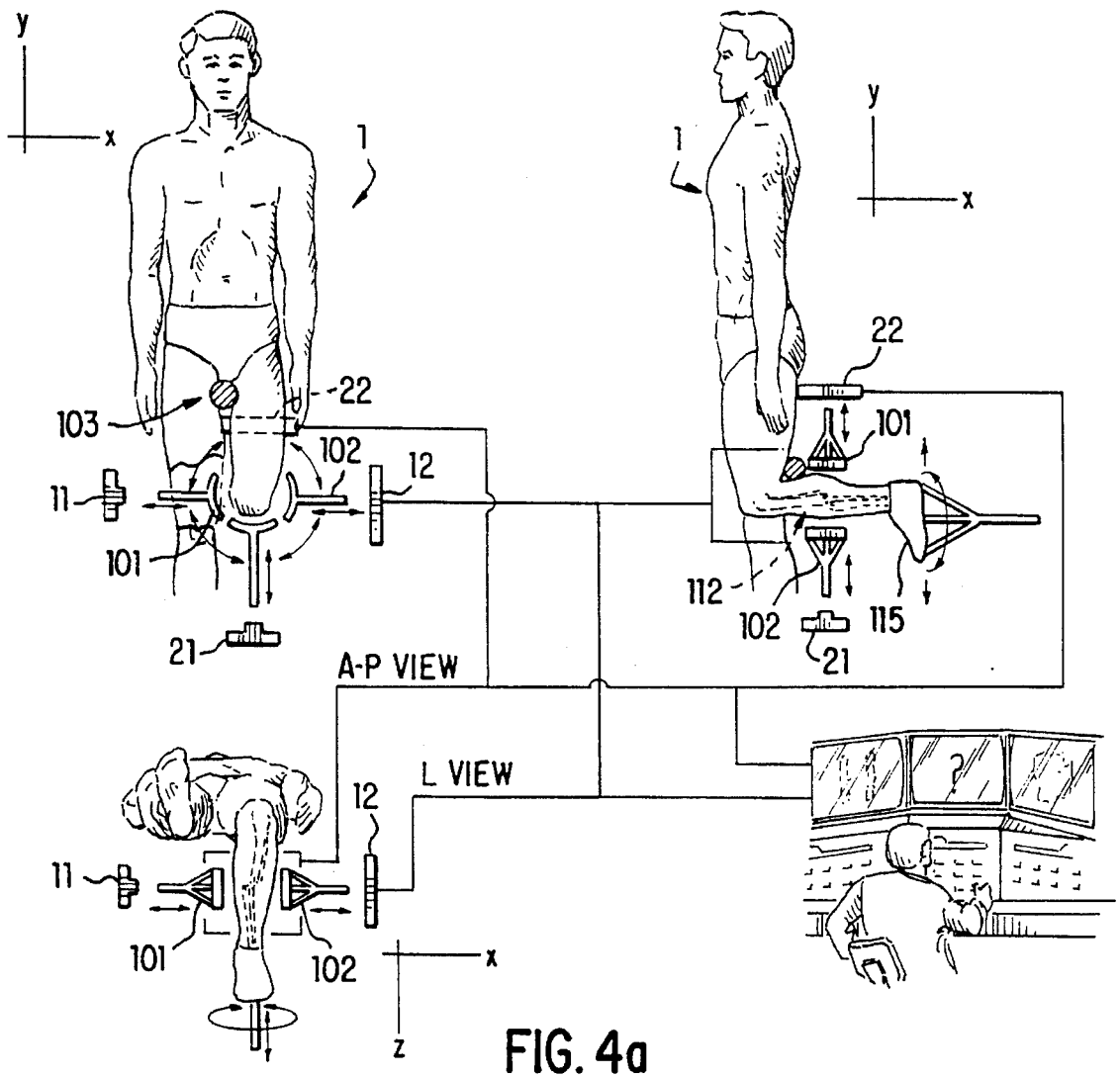
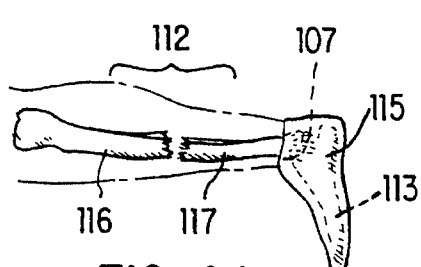
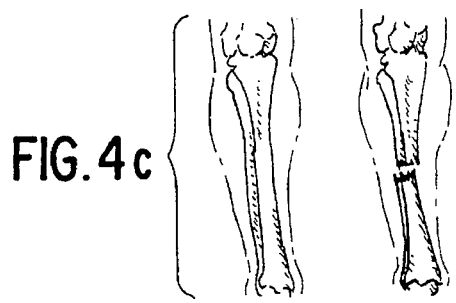
FIG. 4b
FIG. 4a
FIG. 4c
FIG. 4d

ORTHOPEDIC ROBOT AND METHOD FOR REDUCTION OF LONG-BONE FRACTURES

FIELD OF THE INVENTION

The invention relates to the field of the reduction of bone fractures. In particular, it relates to a method and apparatus which allow a physician to remotely reduce bone fractures with improved accuracy and less complications. It furthermore allows the procedure to commence with continuous x-ray monitoring but without the need for the physician to be exposed to excessive x-ray radiation. As such, it is also useful in eliminating needless open surgeries on such fractures.

BACKGROUND OF THE INVENTION

Bone fractures are very common. The National Health Interview Survey (1985–1988) showed an average annual incidence of 1.4 million persons with long bone fractures. The National Ambulatory Medical Care Survey indicated 3.5 million long bone fractures in 1985.

When a bone fracture occurs, the bone is usually displaced from its original alignment. This may occur in a number of ways, which are described in the following section.

Types of Bone Fractures

When a bone is fractured, the displacement of the bone from the original alignment typically takes one or more of the following forms: shortening or overlapping, rotation, lateral shift, angulation, and/or separation. The two segments of the broken bone are referred to as the proximal end and the distal end, with the proximal end being that which is closest to the heart. In general, the proximal end is held fixed while the distal end is moved to match the proximal segment for the actual reduction.

When shortening or overlapping occurs, the bone ends overlap each other, and the length of the broken bone is shorter than that of an unfractured bone.

Rotation occurs when the distal bone segment rotates along its longitudinal axis. When this happens, the diameter and contour of the fractured bone ends will not generally be equal.

A lateral shift refers to a displacement of the bone ends perpendicular to the bone's longitudinal axis by some shift distance.

Angulation occurs when the broken bone ends no longer form the same angle as that of an unbroken bone.

Finally, and most rarely, separation occurs when the fractured ends are separated and are apart from each other in a direction parallel to the bone's longitudinal axis. It occasionally happens as the result of a traction procedure.

Treatment of Bone Fractures

The repair of a broken bone generally involves the processes of reduction, immobilization and fixation, and physical therapy. Reduction refers to the technique whereby the broken bone ends are brought back into alignment. Once reduced, the fracture undergoes immobilization and fixation, which stabilize the reduced fracture during the healing process. Immobilization includes casting, splinting, and bracing of a stable fracture. Fixation includes closed and open internal fixation, and external fixation for unstable fractures. Finally, physical therapy recovers the functions of the limbs after the reduction and immobilization/fixation are completed.

Previous and current methods of setting such fractures are replete with limitations. For example, if the medical team sets the fracture while a fluoroscope monitors progress, the medical team is exposed to certain amounts of x-ray radiation, even despite the use of heavy leaded aprons. Such exposure has been shown to induce aplastic anemia, leukemia, other solid malignant tumors, and inhibition of the reproductive function.

If a fluoroscope is not used, a series of x-ray films must be taken and repeated manual reductions may be needed to secure a proper alignment. This creates a high risk of additional damage to surrounding vessels, nerves, and soft tissues with possible complications to patients, such as mal-union, non-union, paralysis, or ischemia syndrome.

Another limitation is the practical difficulty of immobilizing a bone fracture and applying a cast or splint while at the same time holding the bone ends in alignment. This is particularly true as full recovery of the limb's function requires almost perfect reduction, which in turn requires the physician's manual dexterity to be accurate to within a few millimeters.

A further limitation with current systems is the use of one-plane x-ray films or fluoroscopic views. Such images do not allow the physician to accurately estimate the three-dimensional displacements of the fracture. For example, a physician often has to make an incision into a limb to directly observe the reduction. This additional damage to the patient may result in complications such as infections, delayed unions, non-unions, and other soft tissue injuries.

A still further limitation is the dependence of the success of the fracture reduction on the individual physician's strength, skill, sensitivity, and experience, all of which may vary widely.

Finally, it is worth noting the heavy labor-intensiveness of current systems for bone reduction. In particular, a physician is required as well as at least two assistants. Also, an anesthesiologist and an x-ray technician are necessary.

Systems that provide mechanisms for assisting physicians in bone procedures have been described in the prior art. As an example, U.S. Pat. Nos. 4,979,949, 5,154,171, and 5,236,432, all issued to Matsen III et al., include controller-driven robots which control tools used for bone operations. However, these patents do not describe a system which can grasp and manipulate the bone itself. Additionally, they do not include fluoroscopes for continuous monitoring of the status of the bone, nor do they include types of safeguards, such as limb tension monitoring and automatic cessation of reduction procedures, as does the present invention.

U.S. Pat. Nos. 4,558,697, 5,013,317, 4,485,815, and 4,471,768 are also directed towards bone grips or other devices. However, they are deficient for even more reasons, such as reduced accuracy or the need for physician exposure to the x-ray beam.

There is a need for an x-ray based orthopedic surgical robot that can, with great accuracy, reduce fractures of bones such as these: radius, ulna, humerus, tibia, fibula, and femur. There is further a need for a system which can allow a physician to monitor the x-ray image outside the x-ray shield and operate a remote control to direct a robot to reduce the bone fracture using the robot's hands. This would minimize the exposure of physicians to excessive radiation as well as provide a convenient holding block for limbs while the fracture is immobilized via a cast or splint. There is still further a need for a system which can give the physician precise information on the three-dimensional displacements of the fractured bones. Such a system may even provide the physician with suggestions on what steps should be taken to reduce the fracture. Finally, there is a need for a bone reduction system which reduces the dependence on individual physicians' skill and experience, while at the same time also reducing the overall number of professionals needed during the reduction operation.

SUMMARY OF THE INVENTION

These needs and others are met by the apparatus and method according to an embodiment of the present invention. An apparatus is provided that can reduce bone fractures. The apparatus includes an x-ray system having at least two x-ray generators and at least two cameras, which are coupled to an imaging system for the x-ray system. The x-ray system images body tissues which are held in place by a robotic manipulator. The manipulator may be in the shape of a cuff, a glove, a shoe, or in the shape of a shallow "U". The manipulator may advantageously be made of an x-ray transparent material. The robot and manipulator may be driven by a robot controller. The system also may include a safeguard system which rapidly ceases robot movement upon command of a sensor.

The safeguard sensor senses the tension in a limb through the robot manipulator, and may be made to automatically stop the robot motion and/or allow a physician to stop the motion. Additionally, an alarm may be sounded when an error is detected.

A method is also provided for the fixation of bone fractures. This method includes taking a first continuous x-ray image of a fractured bone at approximately the point of fracture. A second x-ray image is also be taken at approximately the same point, but at a predetermined angle from the first. This angle may advantageously be 90°. To allow the physician to compare the fractured bone to an unfractured bone, third and fourth x-ray images are taken of an unfractured bone and stored. This unfractured bone is advantageously the same type, size, and shape as the fractured bone. For example, if the patient's left femur is fractured, the right femur may be advantageously used as the normal or unfractured bone. The third image is taken at approximately the same angle as the first image, and the fourth image is taken at approximately the same angle as the second, so as to allow a direct comparison to be made.

The fractured limb is then grasped. For certain types of fractures, one robotic manipulator or hand may hold each side of the fractured bone. Alternatively, for other types of fractures, the manipulator or hand may grasp the entire bone at the point of fracture or on just one side of the point of fracture.

At this point, it is important to clarify the lexicography of a bone fracture. A long bone, as it primarily discussed here, has a proximal end and a distal end. The proximal end is generally the end of the bone nearest to the heart, while the distal end is the end of the bone farthest away from the heart. These proximal and distal ends are the bone ends that meet at the joints. For example, the proximal end of the femur is the ball-type bone end that meets the socket-type hip joint. On the other hand, the distal end of the femur is the end of the femur nearest the knee joint. When a bone fracture occurs somewhere along the shaft of a long bone, the long bone is effectively broken into a number of pieces. For simplicity, we consider the situation where the bone is broken into two pieces. While the bone's distal end and proximal end remain the same, there is now present a proximal and distal side of the fracture. The proximal side is the side containing the proximal end and the distal side is the side containing the distal end. The proximal end of the distal side is, by definition, one of the fractured bone ends. Conversely, the distal end of the proximal side is the other of the bone ends. The manipulator or hand moves the fractured bone while the first and second images are monitored. Typically, the bone would be imaged by the x-ray system for a short time, moved an incremental distance, and then imaged again. The process would be repeated until the bone reduction was completed. In this way, the bone could be moved slowly and incrementally while minimizing x-ray exposure to the patient. The most advantageous position for the fractured bone may be determined visually by the physician or by image analysis after all four images are digitized. Of course, the first and second images are monitored intermittently during the procedure while the third and fourth images are advantageously taken and stored prior to the reduction procedure. The angle between the first and second images and between the third and fourth images is kept constant by merely the utilization of the same set of x-ray generators and cameras, as well as the same structure connecting them. To allow a direct comparison of the first image with the third image, the x-ray system, including both generators and cameras, is rotated about the point of fracture until the proximal end of the fractured bone (the end nearest the heart), as given by the first image, appears the same as the proximal end of the unfractured bone, as given by the stored image. Due to the difficulty of obtaining L (lateral) views of the proximal bone end, only the A-P (anterior-posterior) view is used for this part of the procedure. Once the actual reduction procedure is commenced, the differences between the images are monitored after each successive robot movement until both images of the fractured bone appear substantially the same as both images of the unfractured bone, taking into account right/left differences, etc. At this point, the physician sets the fractured bone, and may even leave the robot hand, which can be made disposable, in the splint or cast.

In a more refined embodiment, first and second signals are generated proportional to the differences between the first and third images, and between the second and fourth images, respectively. Incremental movements of the robot hand may then be made such that the values of these signals are minimized. A suggested direction can also be generated corresponding to the direction which, if the robot hand were to move in that direction, the greatest reduction in the value of the signals may occur. As used in this sense, the term "direction" encompasses not only straight movements in three dimensions but also rotational movements. The suggested direction may be transformed so that a particular reduction plan, or part of a plan, is given to the operating physician via a display.

The first and third images may be advantageously A-P views, while the second and fourth may be L views.

Occasionally, fractures occur where both the right and left type of a bone are fractured. For example, both femurs may be fractured. These fractures are termed "bilateral" fractures. In this case, where no unfractured bones are available for comparison, the physician could reduce the bone fracture until, in his or her view, the reduced fracture appears to be correctly set. Of course, in this situation, the physician has to rely exclusively on the images of the fractured bones from the x-ray system. The computerized functions of the image analyzer might still be used, but with default values inserted for the otherwise measured parameters. Such default values might be that the shift distance and overlap equal zero, etc.

According to an embodiment of the present invention, the robot's movements may be controlled by a robot controller.

The orthopedic movements could be any or all of traction, counter-rotation, bone pushes, anti-angulation, and impaction.

According to another embodiment of the present invention, just one x-ray generator and camera may be used. Comparison to an unfractured bone is still possible, as the image of the unfractured bone could again be taken prior to the reduction procedure. However, the use of only one x-ray would inhibit the determination of the precise location of the fracture in space. Thus, more physician monitoring would be necessary to ensure the accurate reduction of the bone fracture.

BRIEF DESCRIPTION OF THE DRAWINGS

FIGS. 4a–4d illustrate an arrangement of robot hands for the reduction of tibial and fibular fractures according to an embodiment of the present invention.

DETAILED DESCRIPTION

Figure 1B:
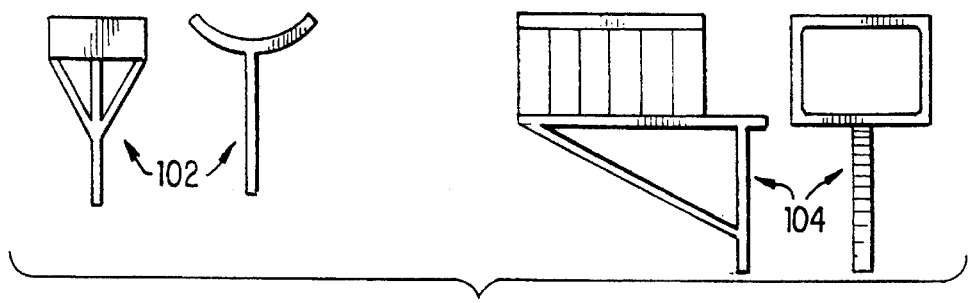
FIGS. 1a–1d illustrate an arrangement of robot hands for the reduction of humerus fractures according to an embodiment of the present invention.

The apparatus and method of the present invention allow the physician to monitor an x-ray image outside of an x-ray shield so as to minimize the physician's exposure to the potentially harmful radiation. The apparatus and method further allows for enhanced accuracy and reduced complications. To reduce a bone fracture, the attending physician could use a remote control device to direct a robot, or may alternatively control the robot via input commands provided to a computer.

Methods and Priority of Reduction in the Present Invention

The most important part of the reduction procedure is that of traction, in which the distal limb of the fractured bone is held and pulled along the longitudinal axis of the bone to overcome any overlapping and shortening. This step must be performed before any shift or angular displacement can be corrected. However, rotation, lateral shift, and angulation may be improved by traction due to the increase in tension of the soft tissue around the fracture.

In performing traction, it is generally difficult to pull by holding the broken segment itself. Therefore, it is useful to instead hold the bone that is next to the fractured bone, and rely on the ligament attachment connecting the joints to translate the traction motion to the fractured bone, as shown in FIGS. 1d, 2d, 3d, and 4d. For example, the joints may be bent at about 90° and the limb next to the broken limb may be pulled to effect traction.

FIG. 1 shows patient 1 being attended to by an embodiment of the present invention. Patient 1 has a broken humerus 106 connected to an unbroken forearm 105 through ligaments 107 at elbow 63. Broken humerus 106 has a proximal side 61 and a distal side 62. Patient 1 is secured against traction by pole 103 under his or her shoulder. Cuff 104 is used to effect traction by its movement in direction 100. Manipulator hands 101 and 102 serve to push the fractured bone ends during the later procedures. Finally, generators 11 and 21 supply x-rays to cameras 12 and 22, with the angle between the two generators being preferably 90 degrees.

Figure 1A:
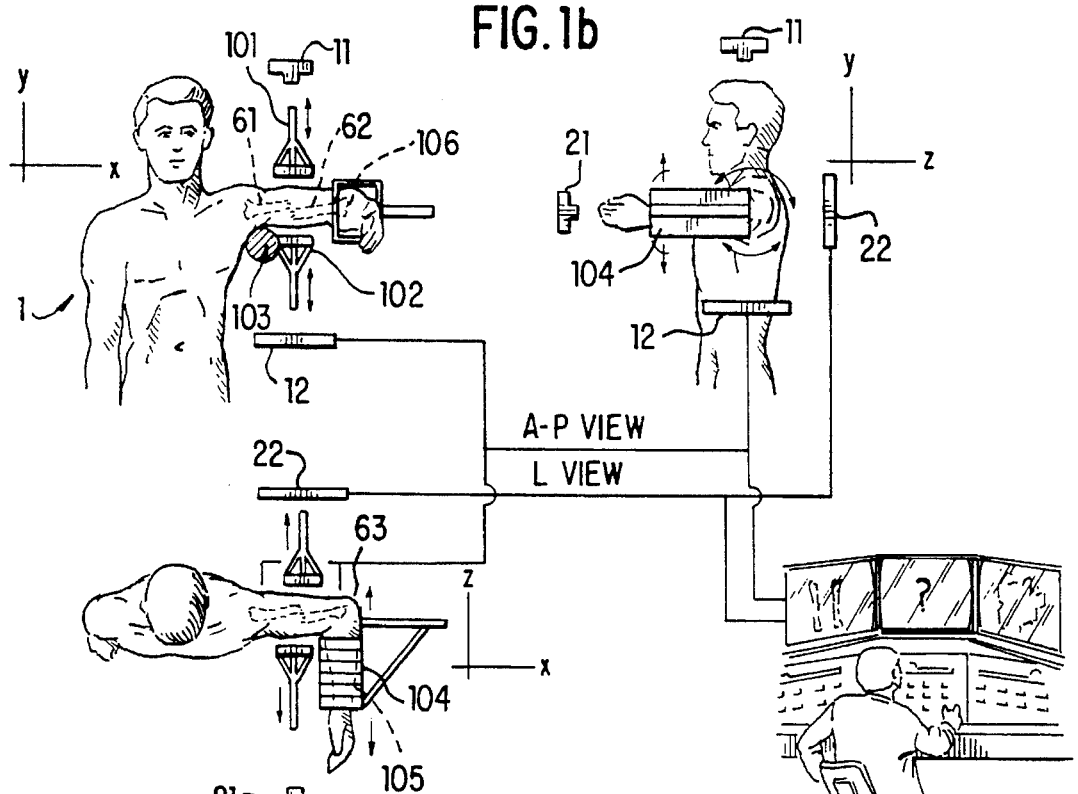
Figure 1C:
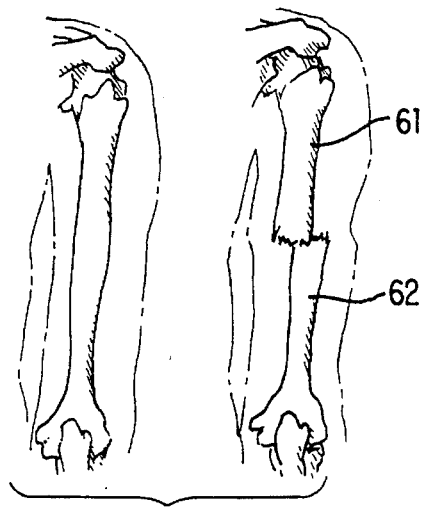
Figure 1D:
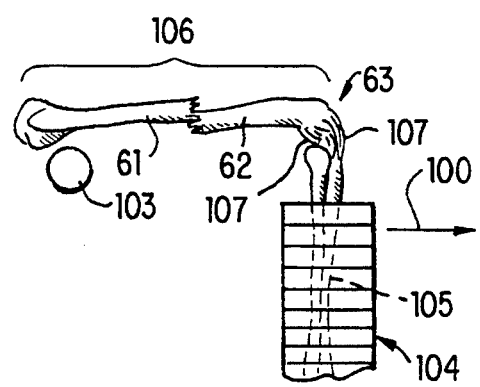

As shown in FIG. 1d, for a fracture of the humerus 106, the physician may bend and fix the shoulder joint via the pole 103 and the elbow joint via the cuff 104, and then may pull on the forearm 105 via the cuff 104 to perform the traction. He or she might do this by placing the humerus 106 over pole 103 to fix the torso position, and placing manipulator cuff 104 over forearm 105. By moving cuff 104 in the positive x-direction, as indicated in FIG. 1 a by arrow 100, traction occurs via translation of the force through ligaments 107.

FIG. 2 shows the procedure for a broken radius and/or ulna 109. The broken bone has proximal side 71 and distal side 72. Distal side 72 is connected to hand 114 via ligaments 107. Hand 114 is placed within glove 108, which may then be pulled for traction or rotated for counter-rotation. As above, manipulator hands 101 and 102 may be used to push bone ends, and the imaging is provided by generators 11 and 21 and cameras 12 and 22.

Figure 2B:
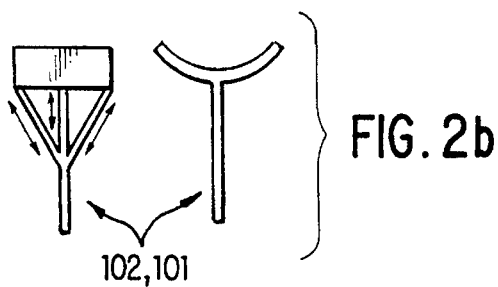
FIGS. 2a–2d illustrate an arrangement of robot hands for the reduction of radius and/or ulna fractures according to an embodiment of the present invention.
Figure 2A:
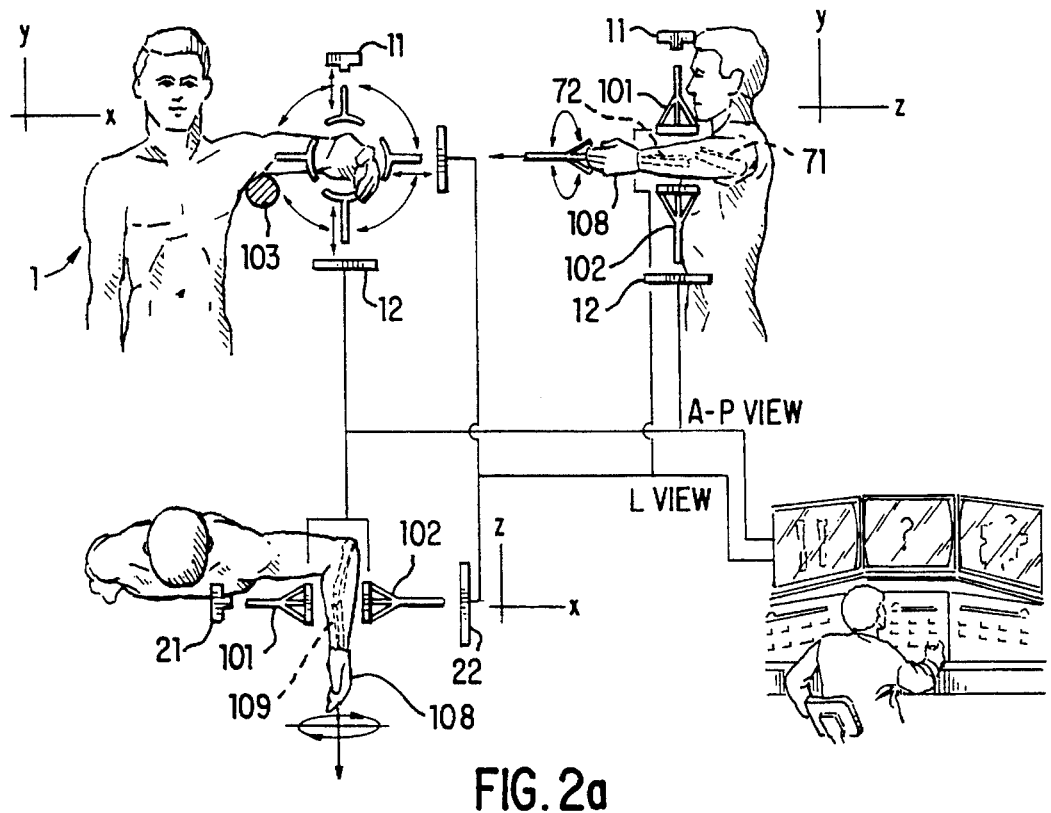
Figure 2D:
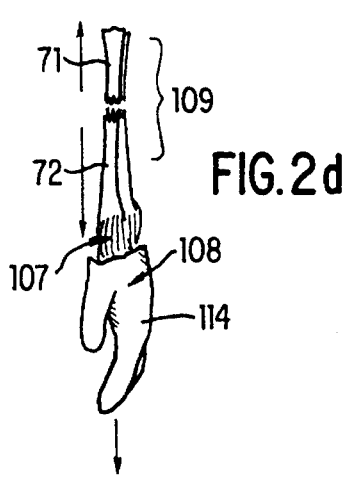
Figure 2C:
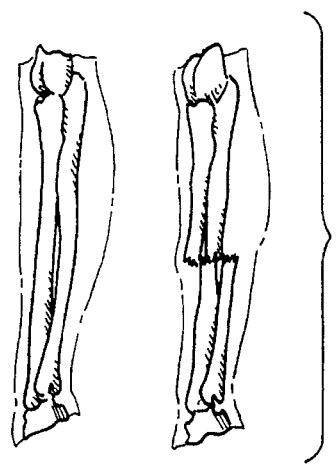

As shown in FIG. 2d, for a fracture of the ulna and/or radius 109, with proximal end 71 and distal end 72, the physician may bend and fix the elbow joint and the wrist joint, and then pull on the patient's hand via a glove manipulator 108 to perform traction. That is, pulling on the glove manipulator 108 effects traction on the fractured limb 109, and more particularly distal end 72, through ligaments 107.

FIG. 3 shows patient 1 with a broken femur 110 connected to an unbroken shin 111 through ligaments 107 at knee 84. Broken femur 110 has a proximal end 81 and a distal end 82. Patient 1 is secured against traction by pole 103 under his or her leg. Cuff 104 is used to effect traction by its movement in direction 115. Manipulator hands 101 and 102 serve to push the bone ends during the later procedures. Again, generators 11 and 21 supply x-rays to cameras 12 and 22, with the angle between the two generators being preferably 90°. As shown in FIG. 3d, pulling on unbroken limb 111 via cuff 104 in direction 115 effects traction on fractured limb 110 via ligaments 107.

Finally, FIG. 4 shows the procedure for a broken tibia and/or tibia 112. The broken bone has proximal end 116 and distal end 117. Distal end 117 is connected to foot 115 via ligaments 107. Foot 115 is placed within shoe 113, which may then be pulled for traction or rotated for counter-rotation. As above, manipulator hands 101 and 102 may be used to push bone ends, and the imaging is provided by generators 11 and 21 and cameras 12 and 22. As shown in FIG. 4d, pulling on unbroken foot 113 via manipulator shoe 115 effects traction on a tibial/fibular fracture 112 through ligaments 107. Occasionally, overtraction may be used to gain space to ease the movement between the two bone ends where surfaces are somewhat irregular.

After traction is performed and the shortening is corrected, counter-rotation may be performed to correct rotation. This is generally performed by rotating the distal limb about the longitudinal axis of the broken bone. This is best accomplished using a manipulator cuff as shown in the Figures by element 104. The manipulator cuff 104 may be tightened a reasonable amount in order to hold the limb firmly. The limb may then be rotated about the joint at the proximal end of the cuff 104. For example, in FIG. 1d, humerus 106 has a proximal end 61 and a distal end 62. If counter-rotation is required, cuff 104 rotates the unfractured forearm 105 about elbow joint 63. Similarly, in FIG. 3, cuff 104 rotates the distal end 82 of fractured femur 110 by rotating the shin 111 about knee joint 84. The special manipulator glove 108 and the manipulator shoe 115 may also be rotated to effect counter-rotation. As such, it is seen that cuff 104 is particularly useful in traction and counter-rotation.

Figure 3B:
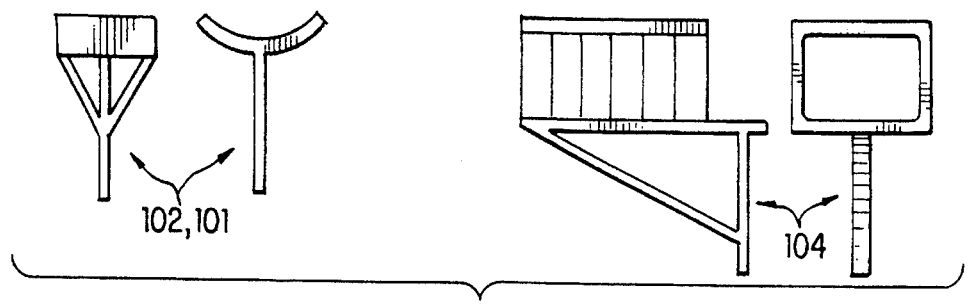
FIGS. 3a–3d illustrate an arrangement of robot hands for the reduction of femoral fractures according to an embodiment of the present invention.
Figure 3A:
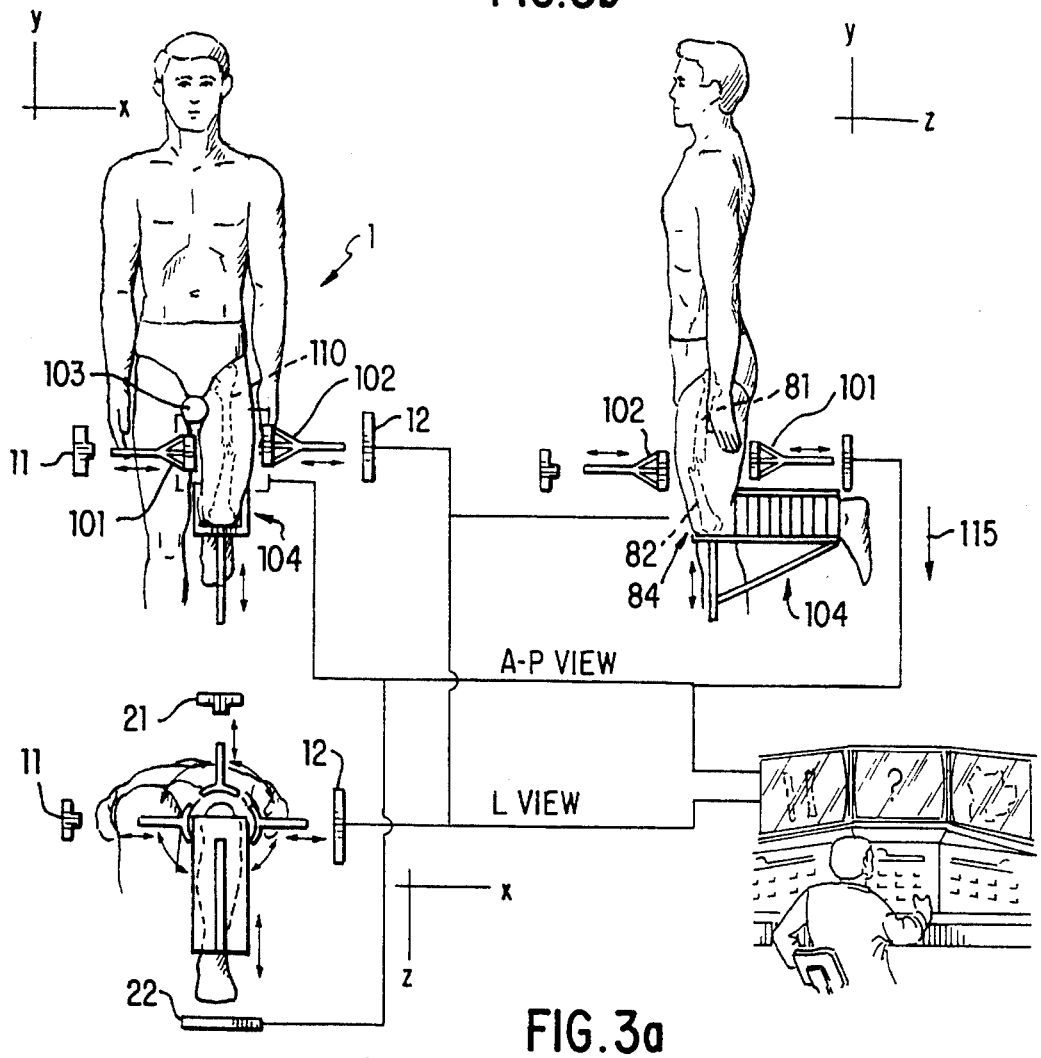
Figure 3C:
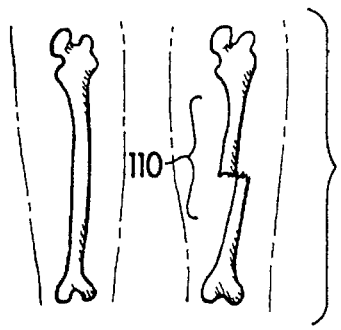
Figure 3D:
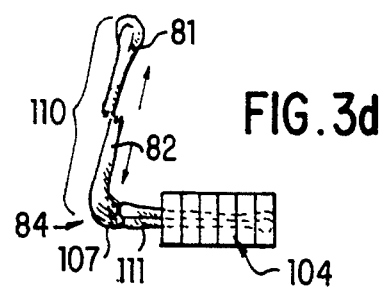

Once shortening and/or rotation have been corrected through traction and/or counter-rotation, the shift displacement can be corrected by pushing the shifted distal bone end to match the proximal end while another robot hand holds the opposite side of the proximal end. This type of procedure utilizes the other variety of manipulator hand, as shown in the Figures by elements 101 and 102. This variety of manipulator is in the shape of a shallow "U", and therefore cannot grasp a bone, but can nevertheless comfortably conform to the bone and push it in a predetermined direction. For example, FIG. 1a shows manipulator 101 pushing the proximal end 61 of the humerus 106 while manipulator 102 pushes the distal end 62. In this way, the proximal end 61 may be brought into alignment with distal end 62. The same is pictured in FIG. 2a where manipulators 101 and 102 are shown pushing proximal end 71 and distal end 72, respectively, toward each other. Alternatively, one manipulator may stay still and the other may push the ends toward each other. Similarly, FIG. 3a shows manipulator 101 pushing proximal end 81 of femur 110 towards the distal end 82 of the same. Finally, FIG. 4a shows manipulator 101 pushing the proximal end of the broken tibia/tibia 112 towards manipulator 102 which is pushing the distal end.

Once the foregoing are complete, antiangulation may be performed. To accomplish this, one robot hand stays at the apex of the fracture while other robot hands push the extremities of the fracture so as to align the distal limb along an axis coinciding with the axis of the unbroken limb. This maneuver, like a bone push, could typically use manipulators such as 101, 102, and cuff 104. While this procedure is not shown in FIGS. 1–4 with respect to a particular long-bone correction, the setup is indicated schematically in FIG. 6 by element 65. It is also apparent that it is the only reduction procedure which takes particular advantage of the use of three robot manipulator hands operating simultaneously.

Finally, impaction or loosening may be performed. This is done by gradually decreasing the strength of traction and allowing the tension of the soft tissue to slowly pull the proximal end to the distal end. Alternatively, cuff 104 may be used to push the distal end of a fractured bone towards the proximal end of a bone. In the procedures shown in FIGS. 2 and 4, a manipulator glove 108 or shoe 115 may be used to push the fractured distal bone ends.

X-Ray System

X-Ray systems of the type which can be utilized in the present invention are generally known. For example, GE and Philips make systems appropriate for implementing the present invention. The x-ray system functions to provide images of the sections of the fractured bones which are of interest. In the disclosed embodiment of the present invention there are at least two generators and two cameras to accomplish this so that three-dimensional positions of fractures may be determined. The two generator/camera systems are preferably at a 90° angle to each other, and revolve, as described later, in unison so as to maintain this 90° angle between views.

As shown in FIGS. 1a, 2a, 3a, and 4a, x-ray generator 11 is located across from camera 12 and affords the L view, while x-ray generator 21 is located across from camera 22 and affords the A-P view. Both generators image the fractured bone, but from an angle which may advantageously be 90° apart from each other. This provides what is termed a biplane x-ray system. In this sense, both A-P and L images of the long bones can be obtained concurrently.

Other combinations of x-ray generators and their placement might be employed to enhance the imaging of the bones.

The x-ray system may be remotely controlled so that it can move and gain whole images of the long bones. In the reduction procedure, generally only A-P views need be used.

The x-ray generators and cameras usually only need to be active when the robot hands 101, 102, and 104 are actually moving the bones. Otherwise, so as to reduce overall exposure, the x-ray generator may be inactive.

Image Analysis and the Knowledge-Based Robot Control Program

The function of the image analysis system is to extract shapes of bone fragments from the x-ray images and determine certain parameters relevant to the reduction. The knowledge-based robot control program controls the robot hands so that orthopedic operations can be performed.

Once the x-ray system generates images of the fractured bones, the images are analyzed. The computer image analyzer may be of a type commercially available from, for example, GE or Philips. Present analyzers are capable of providing, for example, a three-dimensional rendering from a series of two-dimensional pictures. However, the analysis program necessary for the present invention requires certain special features which are unavailable in present systems.

Specific details of bone shift distances, rotation angles, angulation angles, for example, may be used in implementing the present invention. These details may be taken into account in providing a computer program to implement the present invention. The particular parameters necessary for the bone reduction are clear from this specification. The requirements for writing the program are simply that the algorithm compute the required distances and angles necessary for the bone reduction. In particular, the program may compute parameters such as the amount of overlap in millimeters, the degree of internal or external rotation, the lateral shift in millimeters, the degree of angulation, and the distance between the bone ends in millimeters. The analysis program also may provide schematic three-dimensional images on a monitor showing the displacement of bone ends. The analysis program may also suggest commands to the physician via the monitor. These commands could, for example, suggest an appropriate amount of traction to perform. If the physician accepts the suggestion, the analysis program then commands the robot control program to perform the suggested motion via the robot. If the physician does not accept the suggestion, other choices may be provided. These choices could include alternate ways of reduction. Typically, a type of reduction may be suggested as well as a magnitude for the motion, in millimeters or degrees. Also, where appropriate, a direction for the motion can be supplied.

The physician may then select and input any requested data. If confirmed, the robot carries out the commands. If a mistake or error was detected, the physician could stop or undo the robot operations immediately. Also, the safeguard system, described later, could also sound an alarm and stop or undo the robot operations.

Robotic Hands or Manipulators

The actual mechanisms which allow the movement of the robot hands have previously been used in other applications. However, the present invention employs these mechanisms in a medical environment and commands the mechanisms using the results of x-ray image analysis. The function of the robot hands or manipulators is to grasp and/or support the patient's limbs firmly yet comfortably. So as to not inhibit the bone image, the hands may advantageously be made of an x-ray transparent material.

As shown in FIGS. 1b, 2b, 3b, and 4b, the hands can have different shapes so as to best manipulate the patient's fractured bones and to best match the shape of each limb. This includes having hands in the shape of a cuff or a shallow "U". The hands or manipulators can also take the form of gloves or shoes, so as to fit on the patient's hands or feet, respectively. These can be especially utilized in the reduction of radial/ulnar and tibial/fibular fractures.

The hands can advantageously be disposable in an embodiment of the present invention. In this way, after the reduction, the hand may remain to stabilize the reduced bone ends until immobilization, or internal or external fixation is finished. The limb may even be casted or splinted with the robotic hand still in place because the hand may be difficult to remove after casting or splinting is completed.

Finally, the hands may be capable of moving with multiple degrees of freedom. In this way, a large variety of reduction procedures can be realized.

The Method and Apparatus of the Present Invention and Safeguards

Figure 6A:
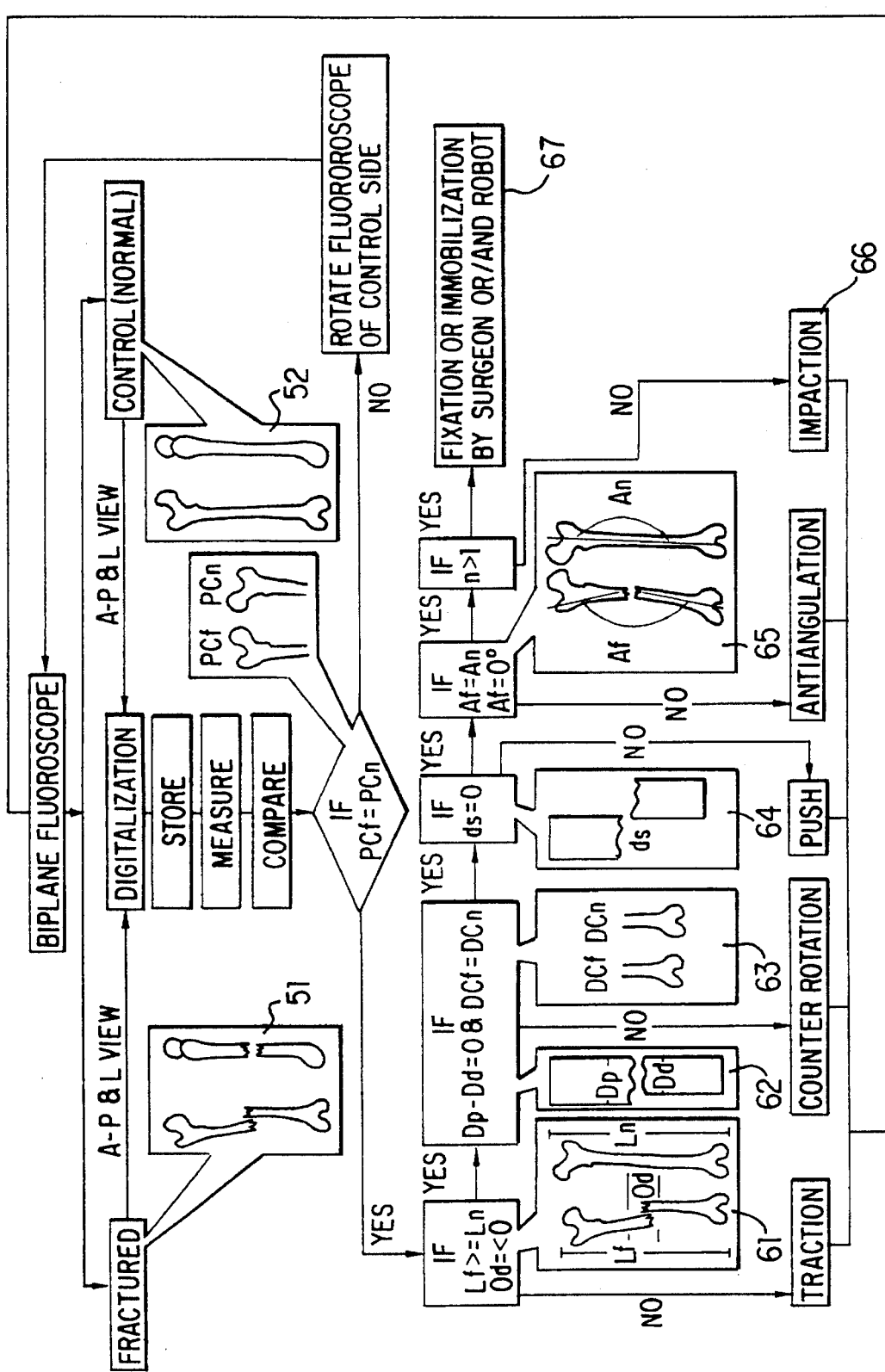
FIGS. 6a and 6b illustrate a flowchart of a method according to an embodiment of the present invention.
Figure 6B:
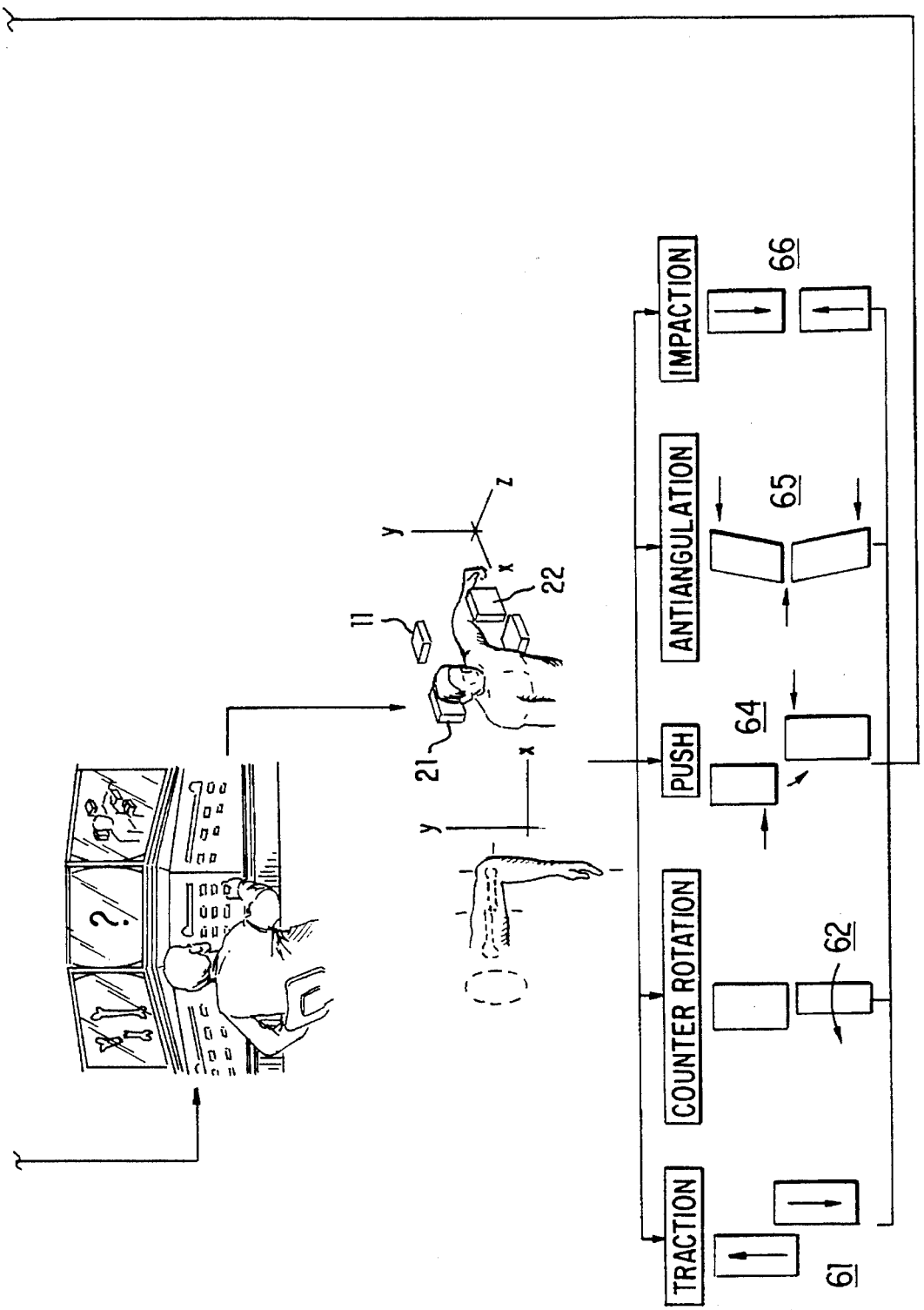

FIG. 6 shows a flowchart of a method according to an embodiment of the present invention. There are two basic stages in this method.

In the first stage, orthogonal x-ray images of the fractured, as well as an unfractured, bone are taken. The series of images of the unfractured bone may be taken and stored well prior to the reduction procedure. The fractured bone image 51 is indicated in FIG. 6, as is the unfractured bone image 52. The two x-ray generator/camera systems, 11 and 12, and 21 and 22, which preferably image the fractured areas from an angle 90° away from each other, rotate together about the fractured area while a signal is generated from each which is directly proportional to the difference between the contour of the proximal end of the fractured limb and the previously measured contour of the proximal end of the unfractured limb. Again, "proximal" refers to the end of the limb located closest to the heart, and "distal" refers to the end of the limb farthest from the heart.

In performing this comparison, there is no need to compare the proximal contours in both the A-P and L views. Only the A-P view comparison is necessary. In fact, the L view is generally unavailable due to the presence of the pelvic bones. When the signal corresponding to the difference between the two views is at a minimum, the contour of the proximal end of the fractured bone is most similar to the previously measured contour of the proximal end of the unfractured bone. The rotation of the x-ray generator/camera systems then cease. At this point, the first image must be at the same viewing angle as the third image and the second image must be at the same viewing angle as the fourth image. In other words, this sets a reference point for the remainder of the procedure.

Once the proximal contours are the same, the second stage begins. This is the stage where the actual robot motion occurs.

Figure 5:
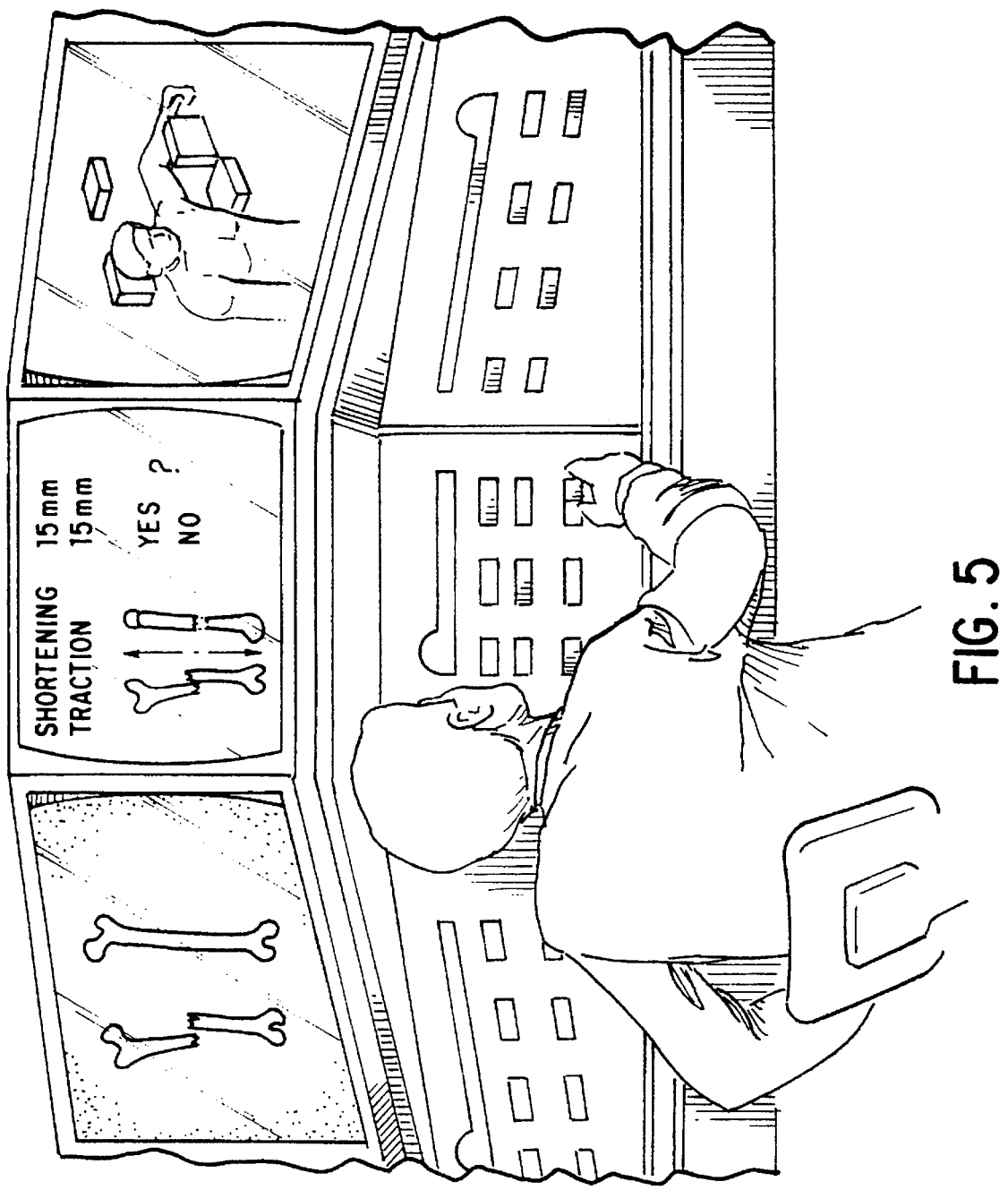
FIG. 5 illustrates an embodiment of a robot control center according to an embodiment of the present invention.

The first motion tested for is traction. In particular, if the image analysis program were to indicate that the overall length of the fractured bone was less than that of the unfractured bone, then some bone overlap must exist. This is indicated in FIG. 6 by the expression that if $L_f$, the length of the fractured bone, is greater than $L_n$, the length of the normal bone, then no traction is necessary. Alternatively, if $O_d$, the distance of overlap, is negative, then no traction is necessary. Otherwise, traction is performed. Of course, the physician may also determine this using visual clues from the x-ray image. For example, the physician may have three computer screens to operate from, as shown in FIG. 5. The first may show fluoroscopic images with various parameters and directions of three-dimensional displacements. The second screen may suggest reduction procedures with appropriate descriptive remarks. The third may give a panoramic view of the operating room. However, if the need for traction is deduced, the same is then instituted to pull the fractured ends of the limb apart. This action is indicated in the flowchart as traction 61. This traction 61 physically occurs via robot hands pulling the bones apart. The manipulators or hands may be designed so that only one hand is actually necessary to perform traction, i.e., one hand may grasp the limb with a positive grip.

The traction is performed incrementally. That is, a small amount of traction is performed, and then another x-ray image is taken to determine if the above conditions are met. If they are not, another incremental amount of traction is performed and another scan is taken. If the conditions are met, the next step in the procedure is performed.

The next motion tested for is counter-rotation 62 and 63. If the image analysis program or the physician's analysis indicates that the diameter of the proximal end of the fracture, $D_p$, is not equal to the diameter of the distal end of the fracture, $D_d$, as shown in 62, then some amount of rotation must have occurred. Alternatively, or complementarily, if the contour of the distal end of the fractured bone, $DC_f$, is not the same as the contour of the distal end of the unfractured bone, $DC_n$, as shown in 63, then rotation must have occurred. Incremental counter-rotation is then instituted to correct the problem until $D_p$ is equal to $D_d$ and $DC_f$ is equal to $DC_n$.

There are, of course, two ways to counter-rotate the bone to make the contours or diameters equal. The analysis program examines the difference between the diameters and contours of the distal ends of the fractured and unfractured bones. This information allows a particular rotation direction to be judged appropriate. Furthermore, only one way will serve to release the tension in the limb, and the safeguard system tests for this so that the correct direction of rotation is used.

As an example, a safeguard sensor in an embodiment of the present invention carefully measures the tension on the skin or on a muscle as it is transmitted through the robot manipulators. That is, the sensors are not actually on the patient, but are rather on the robot manipulator mechanism so as to feel the tension as the robot manipulator moves. For rotation, a sensor senses the tension in the soft tissue. For traction, a sensor senses for when some predetermined length limit was reached. For bone shifts, the sensor tests for the reduction of tension, perhaps also in the soft tissue. If the tension was measured as rising when the same ought to be decreasing, then an error has occurred and the safeguard system may immediately sound an alarm and return the robot hands to their position prior to the error's occurrence, thus "undoing" the motion. More generally, a normal tension change is such that the tension is reduced during counter-rotation or that the tension is increased during traction or antiangulation. The safeguard system allows such movements. However, if the tension increased during counter-rotation, this would be an abnormal tension change and the safeguard system would not allow such movements. This safeguard system may be similarly utilized in all the motion types.

After the counter-rotation, the first test, for traction 61, is run again. This is to ensure that the results have not been disturbed by the counter-rotation. If they have been, traction 61 is again applied, followed by counter-rotation, if indicated. Once the tests for traction and counter-rotation have been successfully passed, the appropriateness of a bone push 64 is tested for. If a nonzero shift distance, ds, measured perpendicular to the axis of the bone, were indicated by the image analysis program or by the physician's analysis, the bone push would serve to physically push the bones together so that the shift distance was zero. As before, the foregoing tests for traction and counter-rotation would again be run. In essence, all of the previous tests must be passed before the procedure moves to the next step.

Following the bone push, if necessary, is an antiangulation procedure 65. Three robot hands are usually necessary for this procedure, as indicated by element 65 in the lower part of FIG. 6. Anti-angulation is performed until the angle formed by the proximal and distal sides of the fractured limb, Af, is equal to the angle formed by the proximal and distal sides of the unfractured limb, An. Following this, of course, the tests for the foregoing steps, traction, counter-rotation, and bone push, would be run, to ensure that their results were not disturbed by the anti-angulation procedure.

As a last step in the second stage, the physician releases the traction, if applied. If traction was never applied, the image analysis program is used to indicate if an impaction 66 was necessary, typically testing if Od were negative or if Lf were greater than Ln. If traction was applied, the physician may try to release the traction prior to fixation and immobilization. In the case of a stable fracture, the bone ends may simply come together and fixation and immobilization may occur. In the case of an unstable fracture, the bone ends may come together and again overlap. In this case, traction must be applied one more time to pull the bone ends apart, and, in this scenario, traction would be continued during the immobilization and fixation procedure.

A robot and controlling devices, and a method for their use, are provided for the reduction of long bone fractures. An x-ray system images the fractured bones, and compares the retrieved images with that of an unfractured bone, if available. The robot, under direction of a physician, moves the fractured bone ends until the fractured limb appears similar to the unfractured bone. A safeguard system protects against erroneous robot movements. Fixation and immobilization may occur while the robot hands are still holding the bone ends. Using the above system, more accurate bone reductions may be performed, and with less complications. Furthermore, the physician may be located safely out of range of the potentially harmful x-ray radiation during the reduction procedure.

What is claimed is:

1. An apparatus for the reduction of bone fractures, comprising:

an x-ray system for imaging the bone fractures with at least one x-ray generator and one camera:

an imaging system coupled to said x-ray system for accepting image inputs of the bone fractures from said camera and for generating results;

a computer image analyzer for analyzing the results of said imaging system;

a robot with at least one manipulator for moving the bone fractures imaged by said x-ray system and a robot controller to drivingly control said at least one manipulator, said robot controller accepting commands from said analyzer.

2. The apparatus of claim 1, further comprising a sensor and a safeguard system to rapidly cease robot movement upon command of said sensor.

3. The apparatus of claim 2, wherein said sensor senses a tension transmitted through the robot manipulators to sense the tension in a limb.

4. The apparatus of claim 2, wherein said safeguard system includes an operator-operable stop mechanism.

5. The apparatus of claim 2, further comprising an alarm, wherein said safeguard system sounds said alarm when an error is detected.

6. The apparatus of claim 1, wherein said at least one manipulator is radiotransparent.

7. The apparatus of claim 1, wherein said at least one manipulator is in a shape of a cuff.

8. The apparatus of claim 1, wherein said at least one manipulator is in a shape of a shallow "U".

9. The apparatus of claim 1, wherein said at least one manipulator is in a shape of a shoe.

10. The apparatus of claim 1, wherein said at least one manipulator is in a shape of a glove.

11. A method for reducing bone fractures, comprising the steps of:

(a) taking a first x-ray image of a fractured bone at approximately a point of fracture;

(b) taking a second x-ray image of the fractured bone at approximately the point of fracture, said second image taken at a predetermined angle from said first image;

(c) taking a third x-ray image of an unfractured bone, the unfractured bone having substantially the same shape and size as the fractured bone, said third image taken at approximately the same angle as said first image and viewing approximately the same area of bone as the point of fracture;

(d) taking a fourth x-ray image of the unfractured bone at substantially the predetermined angle from said third image, said fourth image taken at approximately the same angle as said second image and viewing approximately the same area of bone as the point of fracture;

(e) manipulating at least one section of a limb containing a fractured bone segment with at least one robotic hand;

(f) monitoring a difference between said first image and said third image and between said second image and said fourth image; and (g) repeating steps (a)–(f) until said first image and said third image are substantially the same and said second image and said fourth image are substantially the same.

12. The method of claim 11, wherein said at least one robotic hand is x-ray transparent.

13. The method of claim 11, wherein said first image and said third image are Anterior-Posterior views.

14. The method of claim 11, wherein said second image and said fourth image are Lateral views.

15. The method of claim 11, wherein the manipulating step is performed by a robot controller operated from a remote control.

16. The method of claim 11, wherein the manipulating step includes applying traction.

17. The method of claim 11, wherein the manipulating step includes applying counter-rotation.

18. The method of claim 11, wherein the manipulating step includes applying a bone push.

19. The method of claim 11, wherein the manipulating step includes applying anti-angulation.

20. The method of claim 11, wherein the manipulating step includes applying impaction.

21. The method of claim 11, wherein said predetermined angle is approximately ninety degrees.

22. The method of claim 11, further comprising the steps of:
   (a) analyzing the difference between said first image and said third image, and generating a first signal directly proportional to said difference;
   (b) analyzing the difference between said second image and said fourth image, and generating a second signal directly proportional to said difference; and
   (c) incrementally moving said at least one robotic hand such that said first signal and said second signal are reduced.

23. The method of claim 22, further comprising the step of:
   (a) generating a suggested direction corresponding to a direction of a greatest decrease in the values of the first and second signals.

24. The method of claim 23, further comprising the step of communticating said suggested direction to an operating physician by way of a display.

25. The method of claim 11, further comprising the steps of taking the images with an x-ray generator and a camera and revolving said generator and camera corresponding to said first image substantially about the point of fracture until a contour of the proximal end of the bone imaged by said first image appears substantially the same as a contour of a proximal end of the bone of said third image.

26. The method of claim 11, further comprising the steps of taking the images with an x-ray generator and a camera and revolving said generator and camera corresponding to said second image substantially about the point of fracture until the proximal end of the bone imaged by said second image appears substantially the same as a contour of a proximal end of the bone of said fourth image.

27. The method of claim 11, wherein step (e) further comprises the steps of:
   (1) grasping a bone distal of the fractured bone with a manipulator;
   (2) manipulating said distal bone using said manipulator such that a reduction procedure is performed on the fractured bone; and
   (3) repeating steps (1) and (2) for different reduction procedures until the fractured bone is successfully reduced.

28. The method of claim 27, wherein said manipulator is a cuff.

29. The method of claim 27, wherein said manipulator is a glove.

30. The method of claim 27, wherein said manipulator is a shoe.

31. A method for reducing bone fractures, comprising the steps of:
   (a) taking at least two x-ray images of a fractured bone at different angles with respect to a fixed reference point and at approximately a point of fracture;
   (b) manipulating at least one section of a limb containing the bone fracture with at least one robotic hand;
   (c) monitoring said at least two x-ray images of the fractured bone;
   (d) repeating steps (a)–(c) until the bone fracture is reduced.

32. An apparatus for reducing bone fractures, comprising:
   an x-ray system for imaging at least one section of a limb containing bone fractures and for taking:
      a first continuous x-ray image of a fractured bone at approximately a point of fracture;
      a second continuous x-ray image of the fractured bone at approximately the point of fracture, said second image taken at a predetermined angle from said first image;
      a third continuous x-ray image of an unfractured bone, the unfractured bone having substantially the same shape and size as the fractured bone, said third image viewing approximately the same area of bone as the point of fracture; and
      a fourth continuous x-ray image of the unfractured bone at substantially the predetermined angle from said third image, said fourth image viewing approximately the same area of bone as the point of fracture;
   at least one robotic hand for manipulating the at least one section of a limb containing bone fractures; and
   an image analyzer coupled to said x-ray system for analyzing said x-ray images and for monitoring a difference between and said first image and said third and between said second image and said fourth image.

33. An apparatus for the reduction of bone fractures, comprising:
   an x-ray system for imaging the bone fractures with at least two x-ray generators and two cameras;
   an imaging system coupled to said x-ray system for accepting image inputs of the fractures from each of said two cameras and for generating results;
   a computer image analyzer for analyzing the results of said imaging system;
   a robot with at least one manipulator for moving the bone fractures and
   a robot controller to drivingly control said at least one manipulator, said robot controller accepting commands from said analyzer.

34. A method for reducing bone fractures, comprising the steps of:
   (a) taking two x-ray images of an unfractured bone with a fixed biplane x-ray system, an angle between said two x-ray images being substantially ninety degrees, one of the images being substantially an Anterior-Posterior view, and digitally storing said images;
   (b) taking two x-ray images of a fractured bone with said fixed biplane x-ray system, one of the images being substantially an Anterior-Posterior view;
   (c) rotating said fixed biplane x-ray system;
   (d) repeating steps (b)–(c) until the Anterior-Posterior view of the fractured bone appears substantially the same as the Anterior-Posterior view of the unfractured bone;
   (e) manipulating at least one section of a limb containing the fractured bone with at least one robotic hand;
   (f) comparing said two x-ray images of the fractured bone with said two x-ray images of said unfractured bone; and
   (g) repeating steps (e)–(f) until the bone fracture is reduced.

35. The method of claim 34, wherein step (e) further comprises the steps of:
   (a) grasping a bone distal of the fractured bone with the at least one robotic hand;

(b) rotating said distal bone using said robotic hand such that the distal bone and the distal end of the fractured bone form a predetermined angle; and (c) applying a force to said robotic hand such that the proximal and distal ends of the fractured bone move away from each other in a direction parallel with the axis of the fractured bone.

36. The method of claim 35, wherein said predetermined angle is approximately ninety degrees.

37. The method of claim 35, wherein said robotic hand is a cuff.

38. The method of claim 35, wherein said robotic hand is a glove.

39. The method of claim 35, wherein said robotic hand is a shoe.

40. A method for reducing bone fractures, comprising the steps of:

(a) taking a first x-ray image of a fractured bone at approximately a point of fracture;

(b) taking a second x-ray image of the fractured bone at approximately the point of fracture, said second image taken at a predetermined angle from said first image;

(c) taking a third x-ray image of an unfractured bone, the unfractured bone having substantially the same shape and size as the fractured bone, said third image taken at approximately the same angle as said first image and viewing approximately the same area of bone as the point of fracture, and storing said third image;

(d) taking a fourth x-ray image of the unfractured bone at substantially the predetermined angle from said third image, said fourth image taken at approximately the same angle as said second image and viewing approximately the same area of bone as the point of fracture, and storing said fourth image;

(e) manipulating at least one section of a limb containing a fractured bone segment with at least one robotic hand;

(f) monitoring a difference between said first image and said third image and between said second image and said fourth image; and (g) repeating steps (a), (b), (e), and (f), in that order, until said first image and said third image are substantially the same and said second image and said fourth image are substantially the same.

* * * * *

UNITED STATES PATENT AND TRADEMARK OFFICE
CERTIFICATE OF CORRECTION

PATENT NO. : 5,546,942
DATED : Aug. 20, 1996
INVENTOR(S) : Zhongman Zhang

It is certified that error appears in the above-indentified patent and that said Letters Patent is hereby corrected as shown below:

| Column | Line | |
|---|---|---|
| 6 | 15 | Change "FIG. 1 a" to --FIG. 1a--. |
| 6 | 48 | Change "and/or tibia" to --and/or fibia--. |
| 7 | 31 | Change "tibia/tibia" to --tibia/fibia--. |
| 13 | 30 | Change "imaged by" to --of--. |
| 13 | 37 | Change "imaged by" to --of--. |

Signed and Sealed this

Twenty-fourth Day of December, 1996

Attest:

BRUCE LEHMAN

Attesting Officer    Commissioner of Patents and Trademarks